(12) United States Patent
Irvin et al.

(10) Patent No.: US 7,528,257 B1
(45) Date of Patent: *May 5, 2009

(54) PROCESS FOR MAKING DI-FUNCTIONAL TETRAZOLE DIOLS TO PRODUCE TETRAZOLE BASE POLYMERS

(76) Inventors: David J. Irvin, 300 W. Cielo Ave., Ridgecrest, CA (US) 93555; Mark H. Mason, 8833 Big Horn, Inyokern, CA (US) 93527

( * ) Notice: Subject to any disclaimer, the term of this patent is extended or adjusted under 35 U.S.C. 154(b) by 561 days.

This patent is subject to a terminal disclaimer.

(21) Appl. No.: 11/151,177

(22) Filed: May 27, 2005

(51) Int. Cl.
*C07D 257/04* (2006.01)
(52) U.S. Cl. .................................................... 548/250
(58) Field of Classification Search .............. 514/381; 548/250
See application file for complete search history.

(56) References Cited

U.S. PATENT DOCUMENTS 7,402,679 B1 * 7/2008 Irvin et al. ................. 548/250

OTHER PUBLICATIONS

Demko et al, J. Org. Chem. 2001, 66, 7945-7950, especially p. 7947, Table 2, compound 2n.*

* cited by examiner

*Primary Examiner*—Golam M. M. Shameem
*Assistant Examiner*—Susannah Chung
(74) *Attorney, Agent, or Firm*—Brian F. Drazich; Charlene A. Haley

(57) ABSTRACT

A process for making energetic cast cured binders by making di-tetrazoles to produce di-functional tetrazole diols for producing tetrazole base polymers. Embodiments of the present invention relates generally to a process for preparation of a monomer including reacting an effective amount of nitrile(s) with inorganic azide and a divalent zinc salt in a first solvent, cooling to room temperature producing a di-tetrazole, purifying the di-tetrazole by recrystallization in a second solvent; and reacting an effective amount of the purified di-tetrazole with a third solvent, a soluble reversible or non-reversible base, and 2-chloro-ethanol, cooling to room temperature producing a di-functional tetrazole diol.

19 Claims, No Drawings

PROCESS FOR MAKING DI-FUNCTIONAL TETRAZOLE DIOLS TO PRODUCE TETRAZOLE BASE POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is a need for novel energetic binders to increase the performance of pyrotechnics, gun propellants, rocket propellants, air-bag gas generator propellants, and explosives. Depending on the application, these materials are typically 3-25% binder by mass. Therefore, improvements to the energy content, mechanical properties, or insensitive munitions properties of the polymeric binder can have significant affects on the performance of the energetic material in question.

In general many pyrotechnics, propellants, explosives are comprised of a polymeric binder that holds one or more energetic solids in a plastic matrix. The polymeric binder serves many roles in these materials. Initially the polymer can aid in processing. In fact, the properties of the polymer will significantly affect how a material is processed, wether it is cast or pressed or extruded. Furthermore, the polymer mechanically holds all the ingredients together, serving as a structural element literally binding together the final material. This role is especially critical in rocket propellants, because cracks and voids in the propellant will lead to motor grain failure, often with catastrophic results. The binder serves many safety functions. The binder physically coats the energetic solids in these materials, this provides a physical buffer to minimize the physical and chemical interaction of reactive solids with each other. This generally lowers the electrostatic discharge, impact, and friction sensitivity of the final material. In some materials, especially rocket propellants, the binder also serves as a fuel when the hydrocarbon polymer is combusted by the oxidizer. However, the binder generally diminishes the performance of explosives with significant binder content, and to increase the energy density of propellants energetic polymers are needed.

While there are energetic binders available (polyglycidyl nitrate (PGN), polyglycidyl azide (GAP), azidomethyl-methyl-oxetane (AMMO), bis(azido-methyl)oxetane) (BAMMO), nitratomethyl-methyloxetane (NMMO), etc.) the safety benefits of increasing binder content are lost because these materials contain either organic azides or nitrate esters (or both). These functional groups are chemically unstable, easily ignited, and generally create reactive fragments on aging. In fact, propellants that utilize nitrate esters generally require expensive monitoring programs throughout their life cycle to insure both adequate safety properties and performance as the propellant ages. The cost of such monitoring is often cited as one reason most modern explosives do not to use nitrate esters as binder materials. Furthermore, the energetic groups are pendant moieties attached to the polymer, but not incorporated into the polymer backbone. This impairs the physical properties of these polymers and causes the formulator to need a higher weight percent of binder in order to achieve adequate coating. In short, there is a need for improved energetic binders to address safety, performance, aging, and processing requirements.

While tetrazoles are somewhat less energetic than azides or nitrates, the bis-alkyltetrazoles of interest are more thermally stable and substantially less chemically reactive. Higher percentages of these binders could be used without anticipating negative safety consequences. Furthermore, the energetic functionality is built into the polymer backbone, minimizing the total moles of pendant atoms. This is anticipated to yield a binder with superior physical properties. A dihydroxy-terminated bis-tetrazole (2,2 Bis(2-ethanol)-1 or 2H-tetrazole)-propane or BETP) has been synthesized on the multigram scale. Initial differential scanning calorimetery (DSC) analysis shows this pre-polymer has promise as an energetic cured urethane binder for explosives and propellants and gas generatos.

U.S. Pat. No. 5,053,086 issued on Oct. 1, 1991 to Henry, et al., which teaches gas generating compositions containing energetic high nitrogen such as ammonium 5-nitraminotetrazole and 5,5'-bitetrazole. This work yielded polymeric binders that are too rigid and "glassy" for the intended application. The chemical structure of the present invention polymers builds more flexibility into the backbone, yielding improved elastomers. Further research by Demko teaches the addition of sodium azide to nitriles to give 1H-tetrazoles in water with zinc salts as catalysts. (Demko, Z. P.; Sharpless, K. B. "Preparation of 5-substituted 1H-tetrazoles from nitriles in water." *J. Org. Chem.* 2001, 66, 7945). This step is only one method to obtain the tetrazole intermediate. Further reaction is necessary to produce the alcohol-based monomers. The addition of the alkyl alcohol is two fold: first, the short alkyl chain adds flexibility, solubility; second, the alcohol group allows for the production of stable polyurethanes. Polymerization of the tetrazole would produce the less stable polyurea.

Tetrazole compounds have application in many fields including, but not limited to, chemistry, ligands, metabolically stable surrogate for a carboxylic acid group, and material sciences including explosives and propellants and air bag gas generators.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

Embodiments of the present invention generally relate to a process for making energetic urethane cured binders by using di-tetrazoles to produce di-functional tetrazole diols for making tetrazole based polymers. Other embodiments of the present invention further relate to a process for preparation of a monomer having the general structure (I) comprising: reacting an effective amount of nitrile(s) with inorganic azide and a divalent zinc salt in a first solvent at a temperature in the

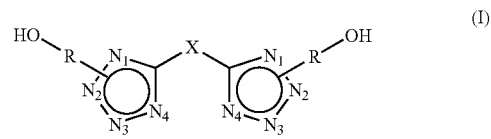

range of about 70° C. to about 170° C. for a time period in the range of about 1 to about 24 hours, wherein the nitrile(s) having the general structure (II), wherein [X] comprises at least one group of alkyls, aryls, and oligoethers; cooling to room temperature producing a di-tetrazole having the general structure (III), wherein [H] is chemically bonded to $N_1$ or $N_2$ position of the di-tetrazole,

(II)

wherein [X] comprises at least one group of alkyls, aryls, and oligoethers; purifying the di-tetrazole by recrystallization in a second solvent; and reacting an effective amount of the purified di-tetrazole

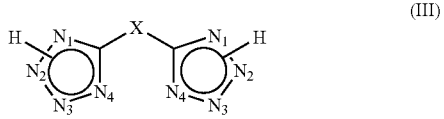

(III)

with a third solvent, a soluble reversible or non-reversible base, and 2-chloro-ethanol at a temperature in the range of about 70° C. to about 150° C. for a time period in the range of about 1 to about 24 hours, cooling to room temperature producing a di-functional tetrazole diol having the general structure (I), where [X] comprises at least one group of alkyls, aryls, and oligoethers, where [R] comprises at least one group of alkyls, aryls, and oligoethers, wherein [R] is chemically bonded to $N_1$ or $N_2$ of position the tetrazole diol (I).

The nitrile(s) utilized include, but not limited to, at least one of dimethyl-malononitrile and malononitrile. When dimethyl-malononitrile is utilized it includes 2,2-dimethyl-malononitrile. In embodiments, the inorganic azide includes at least one of sodium azide, lithium azide, and potassium azide. In the method for making tetrazole diols the divalent salts utilized includes zinc bromide. The first solvent is polar which includes at least one of water, alcohol including 2-propanol, dimethylformanide, dimethylacetamide, and N-methyl pyrrolidinone. The second solvent includes at least one of ethyl acetate and hexane. The third solvent is polar which includes at least one of water, alcohol including 2-propanol, dimethylformanide, dimethylacetamide, and N-methyl pyrrolidinone. Polar solvents are used to insure the products and their intermediates stay in solution during the reaction. The non-polar solvents are used to isolate and/or purify the products. In embodiments of the present invention, a soluble base is utilized. The use of a soluble base insures known stoichiometry and consistent reactivity. The soluble reversible base includes at least one of sodium hydroxide, lithium hydroxide, and potassium hydroxide. The soluble non-reversible base includes at least one of sodium hydride, lithium hydride, and potassium hydride.

When each di-tetrazole is produced it includes its isomer and each di-tetrazole isomer is independent of other di-tetrazole isomers. In embodiments of the present invention, the tetrazole diol is alkylated tetrazole diol and each alkylated tetrazole diol includes its isomers and each alkylated tetrazole isomer is independent of other alkylated tetrazole isomers. In some embodiments, the alkylated tetrazole diol includes di-tetrazole diol. In other embodiments, the tetrazole diol is arylated tetrazole diol and each arylated tetrazole diol includes its isomers and each arylated tetrazole isomer is independent of other arylated tetrazole isomers. Yet still in other embodiments, the arylated tetrazole diol includes di-tetrazole diol or an oligoether tethered diol. In other methods the tetrazole diol produces di-tetrazole diol.

In embodiments of the present invention when the nitrile, 2,2-dimethyl-malononitrile is utilized, the di-tetrazole diol (I) produced is Bis(N-ethanol-5-tetrazolyl)propane. The Bis(N-ethanol-5-tetrazolyl)propane in this embodiment includes at least one of 2,2-Bis(5-(1-N-ethanol-5-tetrazolyl)propane (Ia), 2,2-Bis(5-(2-N-ethanol-5-tetrazolyl)propane (Ib), and 2-(5-(1-N-ethanol-5-tetrazolyl)-2-(5-(2-N-ethanol-5-tetrazolyl)propane (Ic).

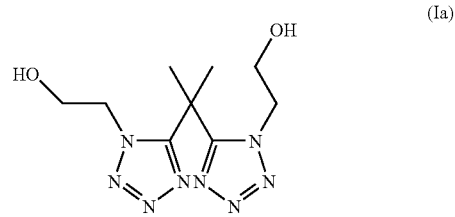

(Ia)

2,2-Bis(5-(1-N-ethanol-5-tetrazolyl)propane

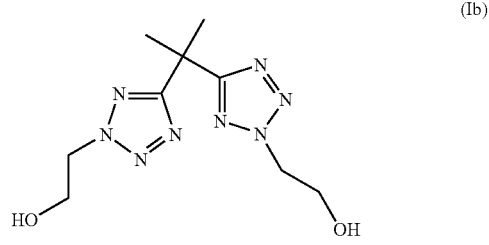

(Ib)

2,2-Bis(5-(2-N-ethanol-5-tetrazolyl)propane

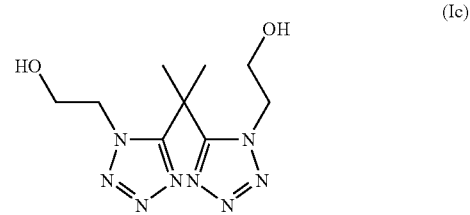

(Ic)

2-(5-(1-N-ethanol-5-tetrazolyl)-2-
(5-(2-N-ethanol-5-tetrazolyl)propane

Also, when embodiments of the present invention include the nitrile, 2,2-dimethyl-malononitrile is utilized, and the purified di-tetrazole (III) produced is Bis(5-tetrazolyl)propane. The Bis(5-tetrazolyl)propane in this embodiment includes at least one of 2,2-Bis(5-(1-[H]-tetrazolyl)propane (IIIa), 2,2-Bis(5-(2-[H]-tetrazolyl)propane (IIIb), and 2-(5-(1-[H]-tetrazolyl)-2-(5-(2-[H]-tetrazolyl)propane (IIIc).

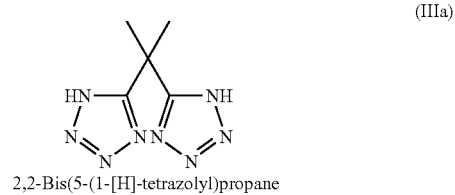

(IIIa)

2,2-Bis(5-(1-[H]-tetrazolyl)propane

-continued

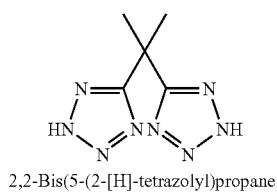
2,2-Bis(5-(2-[H]-tetrazolyl)propane (IIIb)

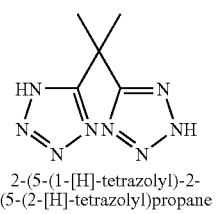
2-(5-(1-[H]-tetrazolyl)-2-(5-(2-[H]-tetrazolyl)propane (IIIc)

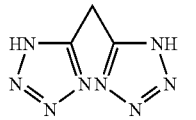
Bis(5-(1-[H]-tetrazolyl)methane (IIId)

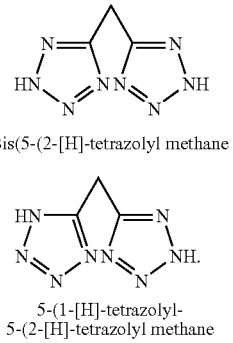
Bis(5-(2-[H]-tetrazolyl methane (IIIe)

5-(1-[H]-tetrazolyl-5-(2-[H]-tetrazolyl methane (IIIf)

In other embodiments of the present invention when the nitrile, malononitrile is utilized, the di-tetrazole diol (I) produced is Bis(N-ethanol-5-tetrazolyl)methane. The Bis(N-ethanol-5-tetrazolyl)methane in this embodiment includes at least one of 2,2-Bis(5-(1-N-ethanol-5-tetrazolyl)methane (Id), 2,2-Bis(5-(2-N-ethanol-5-tetrazolyl)methane (Ie), and 2-(5-(1-N-ethanol-5-tetrazolyl)-2-(5-(2-N-ethanol-5-tetrazolyl)methane (If).

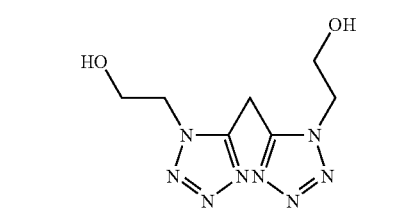
Bis(5-(1-N-ethanol-5-tetrazolyl) methane (Id)

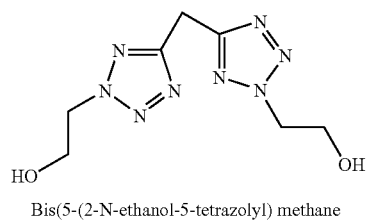
Bis(5-(2-N-ethanol-5-tetrazolyl) methane (Ie)

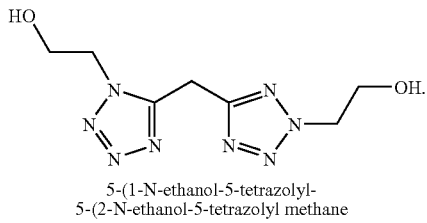
5-(1-N-ethanol-5-tetrazolyl-5-(2-N-ethanol-5-tetrazolyl methane (If)

When embodiments of the present invention include nitrile and malononitrile is utilized, the purified di-tetrazole (III) produced is Bis(5-tetrazolyl)methane. The Bis(5-tetrazolyl) methane in this embodiment includes at least one of 2,2-Bis (5-(1-[H]-tetrazolyl)methane (IIId), 2,2-Bis(5-(2-[H]-tetrazolyl)methane (IIIe), and 2-(5-(1-[H]-tetrazolyl)-2-(5-(2-[H]-tetrazolyl)methane (IIIf).

Experimental Results and Prophetic Examples

The focus of the synthesis was on the new two monomers. Due to materials cost, the same chemistry on malonitrile was tested to produce the diol. For a higher nitrogen content and a lower equivalent weight, the tetra-alcohol was synthesized from 1,1,3,3 tetracyanopropane. The resulting monomer should be polymerized using the current formulation catalyst, triphenyl bismuth and analyzed.

The synthesis and subsequent polymerization of tetrazole-based polyols is a three-step process from which commercially available materials were utilized. Commercial nitroles are converted to the tetrazole using sodium azide and zinc bromide in water (occasionally, 2-propanol is added if the nitrile is insoluble in water) giving good yields (60-95%). The resultant materials are purified by recrystallization (see Demko). In the second step, the novel idea of utilizing water, sodium hydroxide, and 2-chloro-ethanol in high yields (~75%) with the subsequent monomers being purified by column chromatography. At this point the equivalent weight of the alcohol is determined and the polymerization is optimized. A performance test on this transformation using dimethylmalonitrile to produce test di-tetrazole diol.

Example of Polymerization

Difunctional Tetrazole with Difunctional Isocyanate

In a glass vial equipped with a stir bar, dihydroxy(2,2-dimethyl) bis tetrazole (95 mg), hexamethylene di-isocyanate (60 mg), tetrahydrofuran (5 mL) and dimethylaminopyridine catalyst were combined and stirred at 65° C. for 2 hours, to yield a pale yellow solid rubber. The solid was analyzed by DSC.

Difunctional Tetrazole with Trifunctional Isocyanate

In a glass vial equipped with a stir bar, dihydroxy(2,2-dimethyl) bis tetrazole (200 mg), tri functional isocyanate (Tolunate LV) (98 mg), and dimethylaminopyridine catalyst (20 mg) were combined and stirred at 60° C. for 12 hours, to yield a pale yellow solid rubber. The solid was analyzed by DSC.

Tetrafunctional Tetrazole with Trifunctional Isocyanate

In a glass vial equipped with a stir bar, tetra tetrazole (500 mg), tri functional isocyanate (Tolunate LV) (500 mg), and triphenyl bismith catalyst (50 mg) were combined and stirred at 60° C. for 12 hours, to yield an off-white rubbery foam. The solid was analyzed by DSC.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for preparation of a monomer of formula (I) comprising:

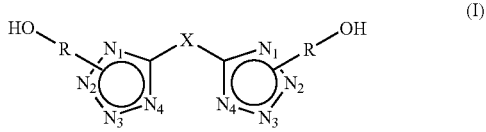

reacting in a first solvent an inorganic azide and a divalent zinc salt with a nitrile of formula (II), at a temperature in the range from about 70° C. to about 170° C. for a time period in the range from about 1 hour to about 24 hours, allowing contact of reactants, wherein "X" is a group consisting of at least one of alkyl, aryl, and oligoethers, to form a first composition;

cooling said first composition to about room temperature to form a second composition including a di-tetrazole of formula (III), wherein "H" is chemically bonded to $N_1$ or $N_2$ of said di-tetrazole;

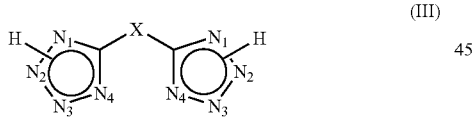

isolating said di-tetrazole by recrystallization or precipitation from a suitable second solvent; and reacting said di-tetrazole in a third solvent with a soluble reversible or non-reversible base and 2-chloro-ethanol at a temperature in the range from about 70° C. to about 150° C. for a time period in the range from about 1 hour to about 24 hours, allowing contact of reactants, to form a third composition;

cooling said third composition to about room temperature to form a fourth composition including a difunctional tetrazole diol of formula (I), wherein [R] comprises at least one group of alkyls, aryls, and oligoethers, wherein "R" is chemically bonded to $N_1$ or $N_2$ of said tetrazole diol (I).

2. The process according to claim 1, wherein said nitrile is at least one of dimethyl-malononitrile and malononitrile.

3. The process according to claim 2, wherein said dimethyl-malononitrile is 2,2-dimethyl-malononitrile.

4. The process according to claim 1, wherein said inorganic azide is at least one of sodium azide, lithium azide, and potassium azide.

5. The process according to claim 1, wherein said divalent zinc salt is zinc bromide.

6. The process according to claim 1, wherein said first solvent is a polar solvent at least one of which is selected from the group of polar solvents consisting of water, alcohol, 2-propanol, dimethylformanide, dimethylacetamide, and N-methyl pyrrolidinone.

7. The process according to claim 1, wherein said second solvent is at least one of ethyl acetate and hexane.

8. The process according to claim 1, wherein said third solvent is a polar solvent at least one of which is selected from the group of polar solvents consisting of water, alcohol, 2-propanol, dimethylformanide, dimethylacetamide, and N-methyl pyrrolidinone.

9. The process according to claim 1, wherein said soluble reversible base is at least one of sodium hydroxide, lithium hydroxide, and potassium hydroxide.

10. The process according to claim 1, wherein said soluble non-reversible base is at least one of sodium hydride, lithium hydride, and potassium hydride.

11. The process according to claim 1, wherein said tetrazole diol is alkylated tetrazole diol.

12. The process according to claim 11, wherein said alkylated tetrazole diol is di-tetrazole diol.

13. The process according to claim 1, wherein said tetrazole diol is alkylated tetrazole diol.

14. The process according to claim 13, wherein said arylated tetrazole diol is di-tetrazole diol.

15. The process according to claim 1, wherein said tetrazole diol is di-tetrazole diol.

16. The process according to claim 15, wherein said di-tetrazole diol (I) is Bis(N-ethanol-5-tetrazolyl)propane, said Bis(N-ethanol-5-tetrazolyl)propane is at least one of 2,2-Bis(5-(1-N-ethanol-5-tetrazolyl)propane (Ia), 2,2-Bis(5-(2-N-ethanol-5-tetrazolyl)propane (Ib), and 2-(5-(1-N-ethanol-5-tetrazolyl)-2-(5-(2-N-ethanol-5-tetrazolyl)propane (Ic);

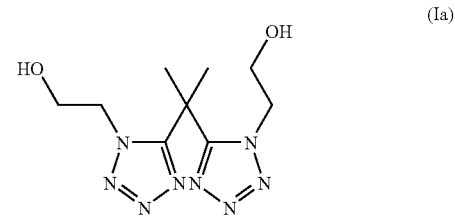

2,2-Bis(5-(1-N-ethanol-5-tetrazolyl)propane

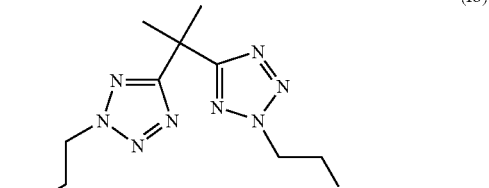

2,2-Bis(5-(2-N-ethanol-5-tetrazolyl)propane

-continued (Ic)

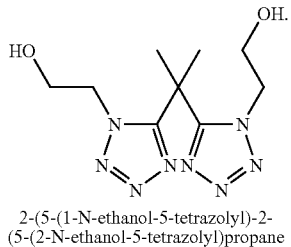

2-(5-(1-N-ethanol-5-tetrazolyl)-2-
(5-(2-N-ethanol-5-tetrazolyl)propane

17. The process according to claim 1, wherein said purified di-tetrazole (III) is Bis(5-tetrazolyl)propane, said Bis(5-tetrazolyl)propane is at least one of 2,2-Bis(5-(1-[H]-tetrazolyl)propane (IIIa), 2,2-Bis(5-(2-[H]-tetrazolyl)propane (IIIb), and 2-(5-(1-[H]-tetrazolyl)-2-(5-(2-[H]-tetrazolyl)propane (IIIc);

(IIIa)

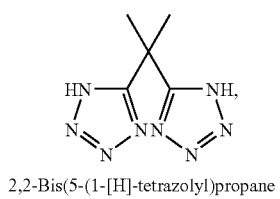

2,2-Bis(5-(1-[H]-tetrazolyl)propane (IIIb)

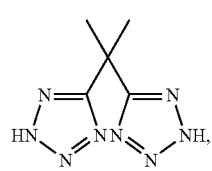

2,2-Bis(5-(2-[H]-tetrazolyl)propane (IIIc)

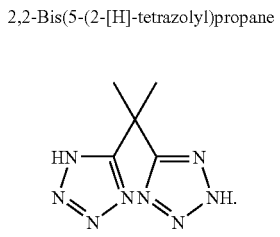

2-(5-(1-[H]-tetrazolyl)-2-
(5-(2-[H]-tetrazolyl)propane

18. The process according to claim 15, wherein said di-tetrazole diol (I) is Bis(N-ethanol-5-tetrazolyl)methane, said Bis(N-ethanol-5-tetrazolyl)methane is at least one of 2,2-Bis(5-(1-N-ethanol-5-tetrazolyl)methane (Ia), 2,2-Bis(5-(2-N-ethanol-5-tetrazolyl)methane (Ib), and 2-(5-(1-N-ethanol-5-tetrazolyl)-2-(5-(2-N-ethanol-5-tetrazolyl)methane (Ic);

(Id)

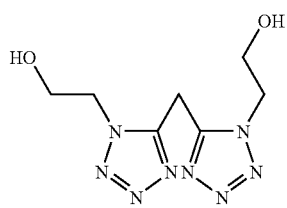

Bis(5-(1-N-ethanol-5-tetrazolyl) methane (Ie)

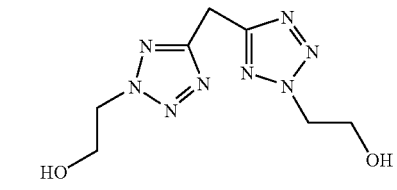

Bis(5-(2-N-ethanol-5-tetrazolyl) methane (If)

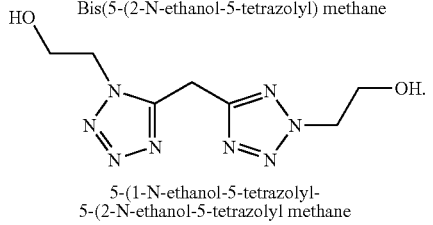

5-(1-N-ethanol-5-tetrazolyl-
5-(2-N-ethanol-5-tetrazolyl methane

19. The process according to claim 1, wherein said purified di-tetrazole (III) is Bis(5-tetrazolyl)methane, said Bis(5-tetrazolyl)methane is at least one of 2,2-Bis(5-(1-[H]-tetrazolyl)methane (IIIa), 2,2-Bis(5-(2-[H]-tetrazolyl)methane (IIIb), and 2-(5-(1-[H]-tetrazolyl)-2-(5-(2-[H]-tetrazolyl)methane (IIIc);

(IIId)

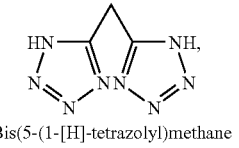

Bis(5-(1-[H]-tetrazolyl)methane (IIIe)

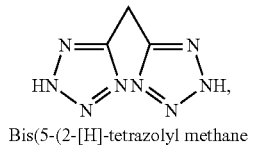

Bis(5-(2-[H]-tetrazolyl methane (IIIf)

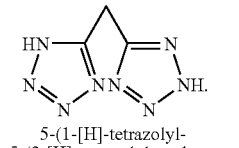

5-(1-[H]-tetrazolyl-
5-(2-[H]-tetrazolyl methane

* * * * *